United States Patent [19]

Anderson

[11] Plant 4,335

[45] Nov. 28, 1978

[54] ALMOND TREE (1-B-475)

[75] Inventor: Frederic W. Anderson, Merced, Calif.

[73] Assignee: The Burchell Nursery, Inc., Modesto, Calif.

[21] Appl. No.: 847,323

[22] Filed: Oct. 31, 1977

[51] Int. Cl.[2] ..... A01H 5/03

[52] U.S. Cl. ..... Plt./30

[58] Field of Search ..... Plt./30

*Primary Examiner*—Robert E. Bagwill
*Assistant Examiner*—James R. Feyrer
*Attorney, Agent, or Firm*—Roger B. Webster

[57] ABSTRACT

An almond tree which is open to dense, medium-to-small size, medium vigorous, medium in quantity of foliage, with medium size, ovate leaves having a crenate margin, and alternate, globose glands, blooms between Ne Plus Ultra and Nonpareil, and a regular and heavy producer of well-distributed oval-to-ovate nuts having a medium-to-late harvest period; the nuts—in harvest after Ne Plus Ultra but before Mission—being of medium-to-small size, soft shell, and with a relatively high percentage of kernel to nut; the variety being particularly characterized by being self-fertile and bearing heavily without pollenizers of any kind.

3 Drawing Figures

BACKGROUND OF THE VARIETY

FIELD OF THE DISCOVERY

Over a substantial number of years I have engaged in an extensive and continuing plant breeding program at my experimental nursery and orchard located near Le Grand, Merced County, Calif.; one purpose of such program being to provide improved varieties of nut trees. The present variety of almond tree resulted from my endeavors in the conduct of such plant breeding program; such variety being embraced by Class 30, Plants, of the U.S. Patent Office MANUAL OF CLASSIFICATION.

PRIOR VARIETIES

Among the existent varieties of almond trees which are known to me are those mentioned herein for the purpose of comparison; to-wit, Ne Plus Ultra, Nonpareil, and Mission (all unpatented).

ORIGIN OF THE VARIETY

The present variety of almond tree was originated by me in my experimental nursery and orchard, located as aforesaid, as a selection from a large number of seedlings which were resultant from planting seeds of unnamed self-fertile almond varieties. Such seedlings were maintained by me under careful and continuing observation, and—in maturity—one of such seedlings (which is the present variety) evidenced certain novel and desirable characteristics for commercial production. I, therefore, selected such one seedling for asexual reproduction.

ASEXUAL REPRODUCTION OF THE VARIETY

Subsequent to origination and selection by me of the present variety of almond tree, I asexually reproduced it by top-working on mature trees in my said experimental orchard, and—in maturity—such reproductions ran true to the original tree in all respects.

SUMMARY OF THE VARIETY

The herein-claimed new and distinct variety of almond tree is open to dense, medium-to-small size, medium vigorous, medium in quantity of foliage, with medium size, ovate leaves having a crenate margin, and alternate, globose glands, blooms between Ne Plus Ultra and Nonpareil, and a regular and heavy producer of well-distributed oval-to-ovate nuts having a medium-to-late harvest period; the nuts—in harvest after Ne Plus Ultra but before Mission—being of medium-to-small size, soft shell, and with a relatively high percentage of kernel to nut; the variety being particularly characterized by being self-fertile and bearing heavily without pollenizers of any kind.

BRIEF DESCRIPTION OF THE DRAWING

The drawing is an illustration, by photographic reproduction in color, of a twig with leaves, nuts out of hull, and kernels out of shell.

DESCRIPTION OF THE VARIETY

The botanical details of this new and distinct variety of almond tree—with color definitions (except those in common color terms) referenced to Maerz and Paul Dictionary of Color—are as follows:

Tree:
- *Density.*—Open to dense.
- *Size.*—Medium to small.
- *Vigor.*—Medium.

Trunk:
- *Form.*—Medium.

Branches:
- *Form.*—Stocky.
- *Texture.*—Medium.
- *Branching habit.*—Medium.
- *Color.*—New wood: Brown to gray. Mature wood: Brown to gray.

Foliage:
- *Quantity.*—Medium.

Leaves:
- *Size.*—Medium to small. Average length — 3". Average width — 1".
- *Shape.*—Ovate.
- *Thickness.*—Medium.
- *Margin.*—Crenate.
- *Petiole.*—Medium length — average ¾". Medium thickness.
- *Glands.*—Number — usually two on petiole, and one or two on blade. Alternate. Globose.

*Color.*—Top side — Medium green (22-L-7). Under side — Lighter green (22-H-6).

Bloom:

*Amount of bloom.*—Heavy.

*Color.*—White.

*Blooming period.*—Medium — between Ne Plus Ultra and Nonpareil.

Crop:

*Bearing.*—Regular bearer.

*Productivity.*—Heavy.

*Distribution of nuts on tree.*—Well distributed.

*Harvest period.*—Sept. 18, 1977. Medium to late, as compared to other varieties. In harvest after Ne Plus Ultra, but before Mission.

*Tenacity.*—Hangs well on tree. Easy to harvest. Easy to hull and shell.

Hull:

*Outer surface.*—Smooth.

*Form.*—Irregular.

*Thickness.*—Thin.

*Flesh.*—Tough.

*Suture.*—Ridged.

*Color.*—Light green.

*Dehiscence.*—Opens freely.

*Splitting.*—Along suture. Down back. At sides. Freely at base.

Nut:

*Size.*—Medium to small. Average length — 1". Average width — ⅝". Average thickness — ½". Average weight — 14 per ounce.

*Form.*—Length/width — Oval to ovate. Width/-thickness — Medium.

*Shell.*—Soft. Thin. Ragged. Outer shell: Adherent to hull. Inner shell: Hard. Poorly sealed.

*Color.*—Beige (12-K-7).

*Pits.*—Small. Numerous. Irregular.

*Base.*—Square.

*Stem scar.*—Small.

*Apex.*—Obtuse.

*Wing.*—Broad. Thin.

*Inner surface.*—Medium colored.

*Percentage of kernel to nut.*—Average — 60%.

Kernel:

*Size.*—Medium. Average length — ⅞". Average width — 9/16". Average thickness — ⅜". Average weight — 31 per ounce.

*Form.*—Length/width — Oval to ovate. Width/-thickness — Medium.

*Base.*—Square to ventrally oblique.

*Stem scar.*—Large to small. Obtuse.

*Apex.*—Obtuse. Blunt.

*Texture.*—Smooth.

*Pellicle.*—Thick to thin.

*Color.*—Medium light brown (14-F-11).

*Number of doubles.*—None to few.

*Defective kernels.*—Very few.

*Flavor.*—Normal.

*Quality.*—Good.

Resistance to insects and diseases: No unusual susceptibilities noted.

The almond tree and its nuts herein described may vary in slight detail due to climatic and soil conditions under which the variety may be grown; the present description being of the variety as grown in the Central Valley of California.

I claim:

1. A new and distinct variety of almond tree, substantially as illustrated and described, which is open to dense, medium-to-small size, medium vigorous, medium in quantity of foliage, with medium size, ovate leaves having a crenate margin, and alternate, globose glands, blooms between Ne Plus Ultra and Nonpareil, and a regular and heavy producer of well-distributed oval-to-ovate nuts having a medium-to-late harvest period; the nuts—in harvest after Ne Plus Ultra but before Mission—being of medium-to-small size, soft shell, and with a relatively high percentage of kernel to nut; the variety being particularly characterized by being self-fertile and bearing heavily without pollenizers of any kind.

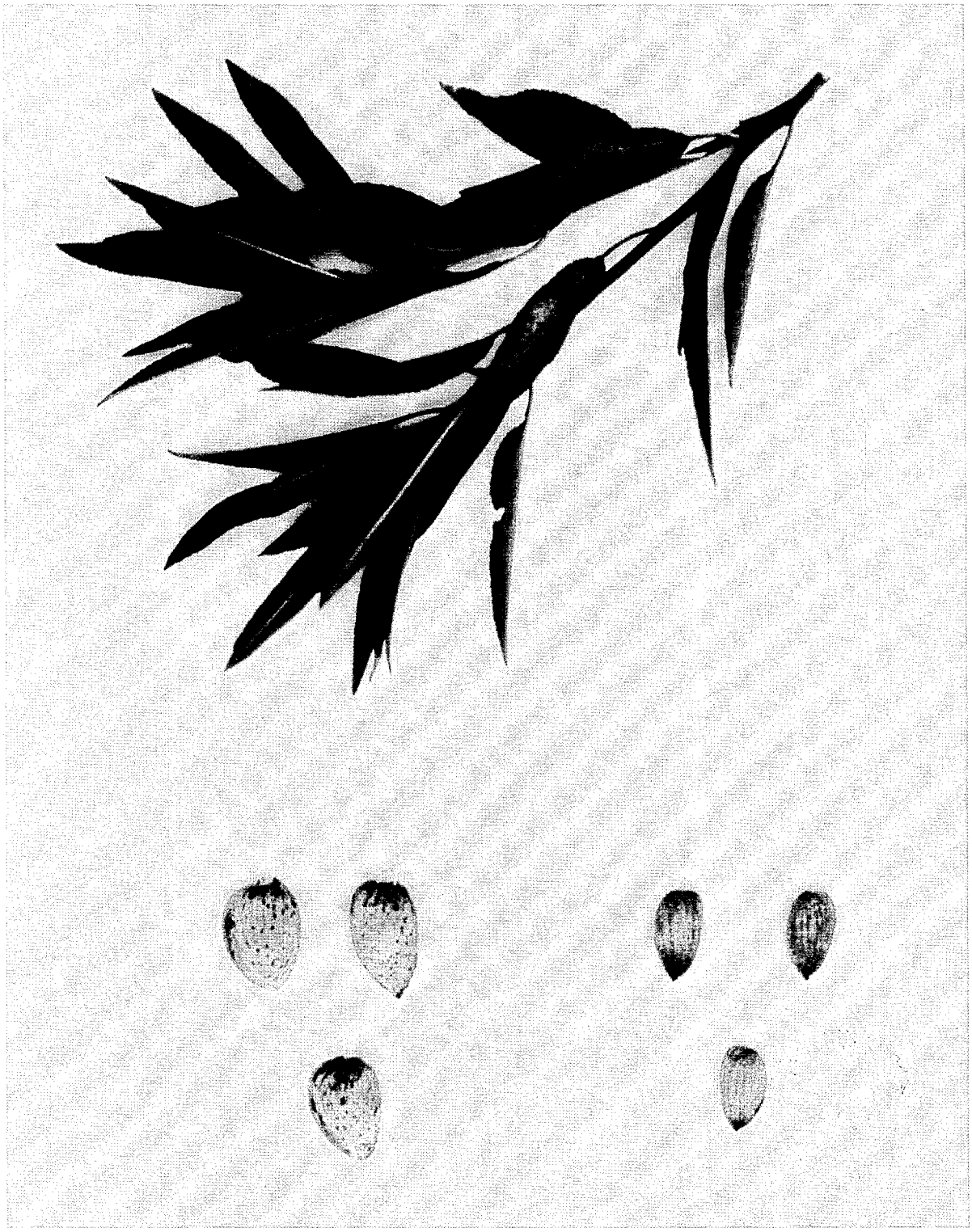

* * * * *